US00PP19251P2

(12) United States Plant Patent
Miyazaki

(10) Patent No.: US PP19,251 P2
(45) Date of Patent: Sep. 23, 2008

(54) ***SENECIO* PLANT NAMED 'SUNSENEBATUBU'**

(50) Latin Name: ***Senecio cruentus*×*Senecio heritieri***
Varietal Denomination: Sunsenebatubu

(75) Inventor: Kiyoshi Miyazaki, Tokyo (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/807,295

(22) Filed: May 26, 2007

(51) Int. Cl.
*A01H 5/00* (2006.01)

(52) U.S. Cl. ..... Plt./480

(58) Field of Classification Search ..... Plt./480
See application file for complete search history.

*Primary Examiner*—Kent L. Bell
*Assistant Examiner*—Annette H Para
(74) *Attorney, Agent, or Firm*—C. A. Whealy

(57) ABSTRACT

A new and distinct cultivar of *Senecio* plant named 'Sunsenebatubu', characterized by its compact, upright and mounded plant habit; freely branching growth habit; freely flowering habit; and daisy-type inflorescences with elliptic-shaped ray florets that are violet blue in color.

1 Drawing Sheet

Botanical designation: *Senecio cruentus*×*Senecio heritieri.*
Cultivar denomination: 'Sunsenebatubu'.

BACKGROUND OF THE INVENTION

The present invention relates to a new and distinct cultivar of *Senecio* plant, botanically known as *Senecio cruentus*× *Senecio heritieri,* and hereinafter referred to by the name 'Sunsenebatubu'.

The new *Senecio* is a product of a planned breeding program conducted by the Inventor in Yamanashi, Japan. The objective of the program is to create and develop new *Senecio* cultivars with uniformly mounded plant habit, freely flowering habit and attractive inflorescence coloration.

The new *Senecio* originated from a cross-pollination by the Inventor in January, 1997 of a proprietary selection of *Senecio cruentus* identified as code number 7S-68c, not patented, as the female, or seed, parent with a unnamed selection of *Senecio heritieri* as the male, or pollen, parent. The new *Senecio* was discovered and selected by the Inventor as a single flowering plant within the progeny of the stated cross-pollination in a controlled environment in Yamanashi, Japan.

Asexual reproduction of the new *Senecio* by terminal cuttings in a controlled environment in Shiga, Japan since March, 2000, has shown that the unique features of this new *Senecio* are stable and reproduced true to type in successive generations.

SUMMARY OF THE INVENTION

The cultivar Sunsenebatubu has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunsenebatusu'. These characteristics in combination distinguish 'Sunsenebatubu' as a new and distinct cultivar of *Senecio:*

1. Compact, upright and mounded plant habit.
2. Freely branching growth habit.
3. Freely flowering habit.
4. Daisy-type inflorescences with elliptic-shaped ray florets that are violet blue in color.

In side-by-side comparisons conducted in Shiga, Japan, plants of the new *Senecio* differ from plants of the female parent selection in the following characteristics:

1. Plants of the new *Senecio* are taller than plants of the female parent selection.
2. Plants of the new *Senecio* have larger inflorescences than plants of the female parent selection.

In side-by-side comparisons conducted in Shiga, Japan, plants of the new *Senecio* differ from plants of the male parent selection in the following characteristics:

1. Plants of the new *Senecio* have larger leaves than plants of the male parent selection.
2. Plants of the new *Senecio* and the male parent selection differ in ray floret color as plants of the male parent selection have darker violet blue-colored ray florets.

Plants of the new *Senecio* can be compared to plants of the *Senecio* cultivar Sunsenebu, disclosed in U.S. Plant Pat. No. 12,104. In side-by-side comparisons conducted in Shiga, Japan, plants of the new *Senecio* differed from plants of the cultivar Sunsenebu in the following characteristics:

1. Plants of the new *Senecio* were smaller than plants of the cultivar Sunsenebu.
2. Plants of the new *Senecio* had smaller leaves than plants of the cultivar Sunsenebu.
3. Plants of the new *Senecio* had smaller inflorescences than plants of the cultivar Sunsenebu.
4. Plants of the new *Senecio* and the cultivar Sunsenebu differed in ray and disc floret color.

BRIEF DESCRIPTION OF THE PHOTOGRAPHS

The accompanying photographs illustrate the overall appearance of the new *Senecio.* This photographs shows the colors as true as it is reasonably possible to obtain in colored reproductions of this type. Colors in the photographs may differ slightly from the color values cited in the detailed description which accurately describe the colors of the new *Senecio*.

The photograph at the top of the sheet comprises a side perspective view of a typical flowering plant of 'Sunsenebatubu' grown in a container.

The photograph at the bottom of the sheet is a close-up view of typical inflorescences of 'Sunsenebatubu'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in Shiga, Japan during the winter in a polyethylene-covered greenhouse and under conditions and practices which approximate those generally used in commercial *Senecio* production. During the production of the plants, day temperatures ranged from 15° C. to 30° C. and night temperatures ranged from 5° C. to 20° C. Measurements and numerical values represent averages for typical flowering plants. Plants were about five months old when the photographs and description were taken.

Botanical classification: *Senecio cruentus*×*Senecio heritieri* cultivar Sunsenebatubu.

Parentage:

*Female, or seed, parent.*—Proprietary selection of *Senecio cruentus* identified as code number 7S-68c, not patented.

*Male, or pollen, parent.*—Unnamed selection of *Senecio heritieri,* not patented.

Propagation:

*Type* .—Terminal vegetative cuttings.

*Time to initiate roots.*—About one week at 20° C.

*Time to produce a rooted cutting.*—About four weeks at 20° C.

*Root description.*—Fine, fibrous; light brown in color.

*Rooting habit.*—Freely branching.

Plant description:

*Plant form/growth habit.*—Compact, upright and mounded plant habit. Inflorescences positioned well above the foliar plane. Vigorous growth habit.

*Plant height.*—About 27.4 cm.

*Plant diameter.*—About 23.4 cm.

*Lateral branches.*—Quantity per plant: Freely branching, about 13 lateral branches per plant; pinching enhances branching. Length: About 21.2 cm. Diameter: About 2.4 mm. Internode length: About 1.9 cm. Strength: Strong. Texture: Sparsely pubescent. Color: 146C.

*Foliage description.*—Arrangement: Alternate, simple. Length: About 6.8 cm. Width: About 6.5 cm. Shape: Roughly cordate. Apex: Acute. Base: Cordate. Margin: Crenate; undulate. Texture, upper surface: Sparsely pubescent. Texture, lower surface: Densely pubescent. Venation pattern: Pinnate; reticulate. Color: Developing and fully expanded foliage, upper surface: 146A; venation, 145C. Developing and fully expanded foliage, lower surface: 48C; venation, 145C. Petiole length: About 3.8 cm. Petiole diameter: About 1.8 mm. Petiole texture, upper and lower surfaces: Sparsely pubescent. Petiole color, upper and lower surfaces: 145C.

Inflorescence description:

*Appearance.*—Daisy-type inflorescence form with elliptic-shaped ray florets. Inflorescences positioned above the foliage, arising from leaf axils. Disc and ray florets developing acropetally on a capitulum. Inflorescences face mostly upright. Freely flowering habit with numerous inflorescences developing over time per plant. Inflorescences persistent.

*Fragrance.*—Faintly scented.

*Flowering response.*—In Shiga, Japan, plants of the new *Senecio* flower continuously from spring to autumn. Inflorescences last about two weeks on the plant.

*Inflorescence bud.*—Height: About 6 mm. Diameter: About 5.4 mm. Shape: Globose. Color: 146C.

*Inflorescence size.*—Diameter: About 4.5 cm. Depth (height): About 1.2 cm. Disc diameter: About 9 mm.

*Ray florets.*—Shape: Elliptic. Length: About 1.8 cm. Width: About 6.3 mm. Apex: Rounded, emarginate or praemorse. Base: Obtuse. Margin: Entire. Texture, upper and lower surfaces: Smooth, glabrous; satiny. Number of ray florets per inflorescence: About 13 in a single whorl. Color: When opening and fully opened, upper surface: 94A. When opening and fully opened, lower surface: 94D.

*Disc florets.*—Shape: Tubular; apex dentate, five-pointed. Length: About 7.8 mm. Diameter: About 1.6 mm. Number of disc florets per inflorescence: About 120. Color, immature: N144B. Color, mature: 95A.

*Phyllaries.*—Quantity per inflorescence: About 13 in a single whorl. Length: About 6 mm. Width: About 1.6 mm. Shape: Lanceolate. Apex: Acute. Base: Fused. Margin: Entire. Texture, upper and lower surfaces: Smooth, glabrous. Color, upper and lower surfaces: 146C.

*Peduncles.*—Length: About 3.4 cm. Diameter: About 1.3 mm. Strength: Strong. Aspect: Mostly upright. Texture: Smooth, glabrous. Color: 146C.

*Reproductive organs.*—Androecium: Present on disc florets only. Anther shape: Ellipsoidal. Anther color: 95A. Pollen amount: Scarce. Pollen color: 22A. Gynoecium: Present on both ray and disc florets. Stigma shape: Bi-parted. Stigma color: 95A.

*Seeds/fruits.*—Seed and fruit development has not been observed on plants of the new *Senecio*.

Disease/pest resistance: Plants of the new *Senecio* have not been shown to be resistant to pathogens and pests common to *Senecio*.

Temperature tolerance: Plants of the new *Senecio* have been observed to tolerate temperatures ranging from about 0° C. to about 30° C.

It is claimed:

1. A new and distinct *Senecio* plant named 'Sunsenebatubu' as illustrated and described.

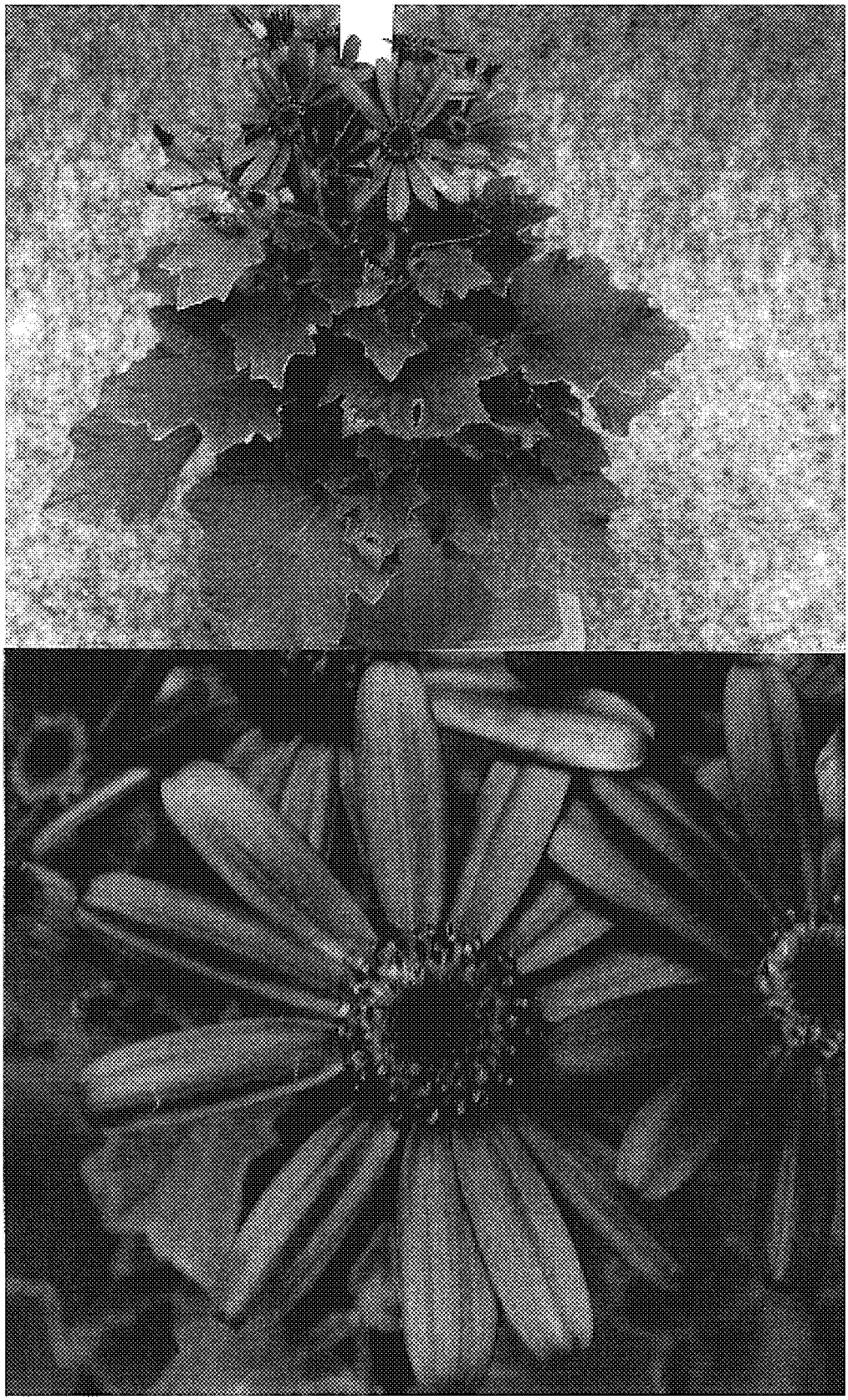

* * * * *